United States Patent
Lim et al.

(10) Patent No.: US 10,702,670 B2
(45) Date of Patent: Jul. 7, 2020

(54) UTILIZATION OF PACKAGING PAPER AS STABILIZATION DEVICE

(71) Applicant: B. Braun Melsungen AG, Melsungen (DE)

(72) Inventors: Wen Jenn Lim, Penang (MY); E-Jen Teh, Penang (MY)

(73) Assignee: B. Braun Melsungen AG, Melsungen (DE)

(*) Notice: Subject to any disclaimer, the term of this patent is extended or adjusted under 35 U.S.C. 154(b) by 125 days.

(21) Appl. No.: 15/513,918

(22) PCT Filed: Sep. 23, 2015

(86) PCT No.: PCT/EP2015/071915
§ 371 (c)(1),
(2) Date: Mar. 23, 2017

(87) PCT Pub. No.: WO2016/046286
PCT Pub. Date: Mar. 31, 2016

(65) Prior Publication Data
US 2017/0246422 A1 Aug. 31, 2017

Related U.S. Application Data (60) Provisional application No. 62/054,828, filed on Sep. 24, 2014.

(51) Int. Cl.
*A61M 25/00* (2006.01)
*A61F 13/00* (2006.01)
(Continued)

(52) U.S. Cl.
CPC ..... *A61M 25/002* (2013.01); *A61B 5/150305* (2013.01); *A61F 13/0008* (2013.01);
(Continued)

(58) Field of Classification Search
CPC ......... A61B 5/150305; A61F 13/00076; A61F 13/0008; A61F 13/0259; A61M 5/002;
(Continued)

(56) References Cited

U.S. PATENT DOCUMENTS 3,035,691 A 5/1962 Rasmussen et al.
3,485,352 A * 12/1969 Pilger ................ A61M 25/002
206/365

(Continued)

FOREIGN PATENT DOCUMENTS

CN 1756513 A 4/2006
CN 103293290 A 9/2013
(Continued)

OTHER PUBLICATIONS

International Search Report and Written Opinion on corresponding PCT application (PCT/EP2015/071915) from International Searching Authority (EPO) dated Dec. 8, 2015.
(Continued)

*Primary Examiner* — Chun Hoi Cheung
(74) *Attorney, Agent, or Firm* — Klein, O'Neill & Singh, LLP (57) ABSTRACT

A medical device packaging assembly includes a cover (10), a medical packaging paper (20), a medical device (50), and an adhesive dressing (30). The cover has a pocket (14) and a perimeter (12) extending from the perimeter of the pocket. The medical packaging paper forms a hermetically tight seal between the medical packaging paper and the perimeter of the cover around the pocket. The medical device is contained in the hermetically sealed pocket along with the adhesive dressing. The adhesive dressing is removably adhered to the medical packaging paper.

32 Claims, 6 Drawing Sheets

(51) Int. Cl.
| | |
|---|---|
| *A61M 5/00* | (2006.01) |
| *B65D 75/32* | (2006.01) |
| *A61B 5/15* | (2006.01) |
| *B65D 85/20* | (2006.01) |
| *B65D 85/24* | (2006.01) |
| *A61F 13/02* | (2006.01) |
| *A61M 25/02* | (2006.01) |
| *B65D 25/10* | (2006.01) |

(52) U.S. Cl.
CPC .... *A61F 13/00076* (2013.01); *A61F 13/0259* (2013.01); *A61M 5/002* (2013.01); *A61M 25/02* (2013.01); *B65D 25/10* (2013.01); *B65D 75/325* (2013.01); *B65D 85/20* (2013.01); *B65D 85/24* (2013.01); *A61M 2025/0266* (2013.01); *A61M 2025/0273* (2013.01)

(58) Field of Classification Search
CPC ..... A61M 25/02; B65D 25/10; B65D 75/325; B65D 85/20; B65D 85/24
USPC .......................... 206/364, 571, 574, 570, 223
See application file for complete search history.

(56) References Cited

U.S. PATENT DOCUMENTS

| | | | | |
|---|---|---|---|---|
| 3,580,254 A * | 5/1971 | Stuart | A61F 13/0203 | 206/441 |
| 4,787,380 A * | 11/1988 | Scott | A61F 13/023 | 206/440 |
| 4,807,613 A * | 2/1989 | Koehnke | A61F 13/0203 | 206/440 |
| 4,915,228 A * | 4/1990 | Johns | A61F 13/0203 | 206/441 |
| 5,099,832 A * | 3/1992 | Ward | A61F 13/023 | 206/441 |
| 5,162,040 A * | 11/1992 | Annett | A61F 13/023 | 128/849 |
| 5,333,753 A * | 8/1994 | Etheredge | A61F 15/001 | 206/441 |
| 5,344,415 A * | 9/1994 | DeBusk | A61M 25/02 | 604/304 |
| 5,407,070 A | 4/1995 | Bascos et al. | | |
| 5,511,689 A * | 4/1996 | Frank | A61F 15/002 | 206/440 |
| 5,695,456 A * | 12/1997 | Cartmell | A61B 17/085 | 206/409 |
| 6,124,522 A * | 9/2000 | Schroeder | A61F 15/001 | 206/440 |
| 6,140,549 A * | 10/2000 | Pompei, Jr. | A61F 15/001 | 206/440 |
| 6,284,941 B1 * | 9/2001 | Cox | A61K 9/7084 | 602/41 |
| 6,769,546 B2 * | 8/2004 | Busch | A61B 17/3401 | 206/366 |
| 7,240,790 B2 * | 7/2007 | Wendel | A45D 37/00 | 206/210 |
| 7,521,586 B2 * | 4/2009 | Schroeder | A61F 15/001 | 206/441 |
| 7,626,071 B2 * | 12/2009 | Masini | A61F 13/00038 | 128/888 |
| 7,650,995 B2 * | 1/2010 | Assie | A61F 13/0203 | 206/229 |
| 8,419,689 B2 * | 4/2013 | Fink | A61M 25/02 | 206/363 |
| 8,893,887 B2 * | 11/2014 | Reinhardt | A61F 13/0008 | 206/440 |
| 2002/0066685 A1 | 6/2002 | Leitch | | |
| 2006/0163101 A1 * | 7/2006 | Assie | A61F 15/001 | 206/440 |
| 2009/0216169 A1 * | 8/2009 | Hansen | A61F 15/001 | 602/48 |
| 2010/0081996 A1 | 4/2010 | Fink et al. | | |
| 2011/0288463 A1 * | 11/2011 | Girasa | A61F 15/002 | 602/57 |
| 2013/0023835 A1 * | 1/2013 | Kuracina | A61B 5/150633 | 604/263 |
| 2014/0034536 A1 * | 2/2014 | Reinhardt | A61F 13/0008 | 206/440 |
| 2017/0232226 A1 * | 8/2017 | Loui | A61M 25/002 | 206/571 |

FOREIGN PATENT DOCUMENTS

| | | |
|---|---|---|
| EP | 1293222 A1 | 3/2003 |
| JP | H08-168532 A | 7/1996 |
| JP | H09-28811 A | 2/1997 |
| JP | 2002-530150 A | 9/2002 |
| WO | WO 98/43691 A1 | 10/1998 |
| WO | WO 00/30579 A1 | 6/2000 |
| WO | WO 2007/091153 A1 | 8/2007 |
| WO | WO 2007/140785 A1 | 12/2007 |
| WO | WO 2014/025590 A1 | 2/2014 |

OTHER PUBLICATIONS

Examination Report on corresponding foreign application (AU Application No. 2015323843) from the Australian Intellectual Property Office dated Jun. 24, 2019.

Office Action on corresponding foreign application (JP Application No. 2017-515133) from the Japanese Patent Office dated May 21, 2019.

Office Action on corresponding foreign application (CN Application No. 201580051851.1) from the National Intellectual Property Administration, P.R. China dated Sep. 4, 2019.

Decision of Rejection on corresponding foreign application (JP Application No. 2017-515133) from the Japanese Patent Office dated Sep. 3, 2019.

* cited by examiner

UTILIZATION OF PACKAGING PAPER AS STABILIZATION DEVICE

FIELD OF ART

The present disclosure generally relates to packaging for medical devices and more particularly to packaging containers for medical devices having multi-use packaging paper.

BACKGROUND

After intravenous (IV) catheterization, it is necessary to secure the IV catheter to the patient's skin to prevent, among other things, movement of the catheter in relation to the blood vessels and premature dislodgement of the catheter. The catheter hub is typically secured by taping the hub to the patient skin through the use of IV dressing and/or medical tape. Of late, there is a shift in preference to using commercially available catheter stabilization device to stabilize the catheter in the patient. These catheter stabilization devices are typically separate products that come in their own packaging. In the midst of a growing awareness towards the environmental effect of medical waste disposal, there is opportunity to improve the stabilization of the catheter while addressing the negative environmental impact of medical waste.

SUMMARY

Aspects of the present disclosure include a medical device package that includes a cover, a packaging paper sealed with the cover, and a device and adhesive dressing sealed inside the cover and packaging paper. In one example, the medical package can comprise a pocket and a perimeter extending from the perimeter of the pocket, a medical packaging paper forming a seal with the perimeter of the cover around the pocket, a medical device contained in the sealed pocket, and an adhesive dressing removably adhered to the medical packaging paper inside the sealed pocket.

The medical device can be a catheter or catheter assembly.

The adhesive dressing can have a shape sufficient to attach and secure the medical device onto a surface. The adhesive dressing can be compatible with EtO and gamma sterilization. The adhesive dressing can be made from a breathable material, a polyester fabric, a polyurethane fabric, or a foam material. The adhesive dressing can have an adhesive material on a side of the adhesive dressing that is removably attached to the medical packaging paper.

The medical packaging paper can comprise a release liner surface contacting the adhesive dressing.

The release liner surface can be a surface coated with polyethylene, polypropylene, fluorocarbons, or silicone release agents.

An adhesive dressing sheet can be attached to the release liner surface of the medical packaging paper, in which case the adhesive dressing is a portion of the adhesive dressing sheet removably adhered to the medical packaging paper. The adhesive dressing can be attached to the adhesive dressing sheet by perforated lines, and can be separated from the adhesive dressing sheet along the perforated lines.

The adhesive material can be a medical grade, pressure-sensitive adhesive and can be an acrylic based, silicone, or hydrocolloid adhesive.

The adhesive dressing can have an opening matching a shape of a protrusion on the medical device.

A perimeter of the opening can be perforated.

A method for securing a medical device to a surface of a patient from a medical device package can include: providing a medical device package, a cover, a medical packaging paper forming a seal around a perimeter of the cover, a medical device contained within the sealed cover, and an adhesive dressing removably adhered to the medical packaging paper inside the sealed cover; removing the cover from the medical packaging paper to access the medical device and the adhesive dressing, removing the medical device and the adhesive dressing from the medical device package; and fixing and securing the medical device on the surface of the patient using the adhesive dressing.

A method of making a medical device package can include providing a cover comprising a pocket and a perimeter extending from the perimeter of the pocket, a medical packaging paper, providing a medical device and an adhesive dressing within the perimeter, the adhesive dressing being removably adhered to the medical packaging paper and forming a seal between the perimeter of the cover around the pocket and the medical packaging paper, the medical device and the adhesive dressing being hermetically sealed.

The medical device can be a catheter or catheter assembly.

The adhesive dressing can have a shape sufficient to attach and secure the medical device onto a surface. The adhesive dressing can be compatible with EtO and gamma sterilization. The adhesive dressing can be made from a breathable material, a polyester fabric, a polyurethane fabric, or a foam material. The adhesive dressing can have an adhesive material on a side of the adhesive dressing that is removably attached to the medical packaging paper.

The medical packaging paper can comprise a release liner surface contacting the adhesive dressing.

The release liner surface can be a surface coated with polyethylene, polypropylene, fluorocarbons, or silicone release agents.

An adhesive dressing sheet can be attached to the release liner surface of the medical packaging paper, in which case the adhesive dressing is a portion of the adhesive dressing sheet removably adhered to the medical packaging paper. The adhesive dressing can be attached to the adhesive dressing sheet by perforated lines, and can be separated from the adhesive dressing sheet along the perforated lines.

The adhesive material can be a medical grade, pressure-sensitive adhesive and can be an acrylic based, silicone, or hydrocolloid adhesive.

The adhesive dressing can have an opening matching a shape of a protrusion on the medical device.

A perimeter of the opening can be perforated.

DESCRIPTION OF DRAWINGS

These and other features and advantages of the present device, system, and method will become appreciated as the same becomes better understood with reference to the specification, claims and appended drawings wherein:

DETAILED DESCRIPTION

The detailed description set forth below in connection with the appended drawings is intended as a description of the presently preferred embodiments of medical device packages and packaging assemblies provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
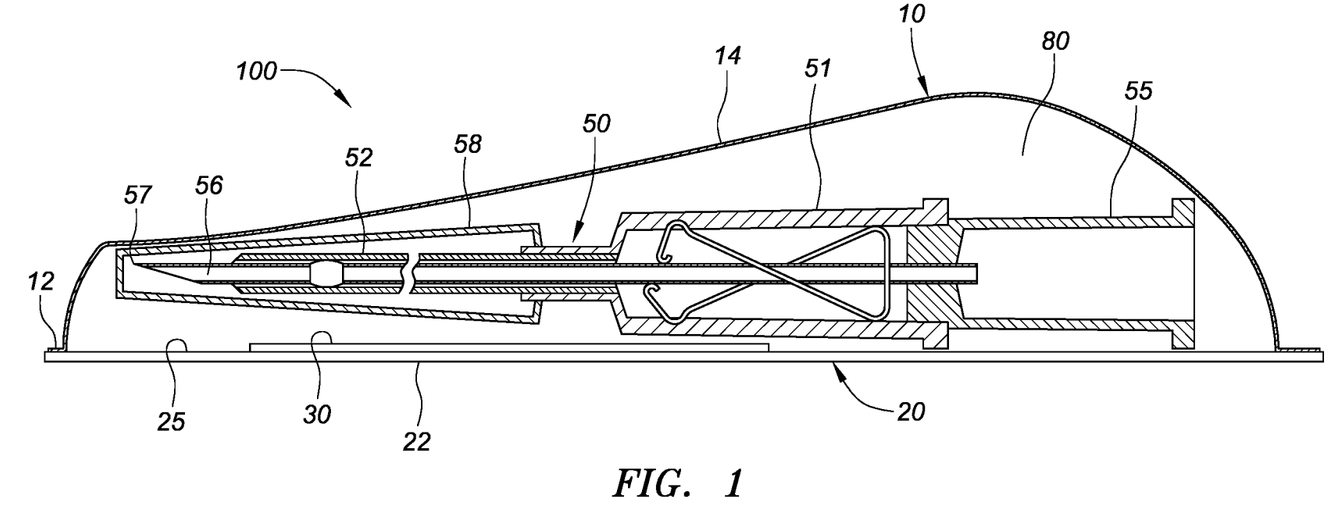
FIG. 1 is a cross-sectional side view of a medical device package provided in accordance with aspects of the present disclosure, the medical device package includes a cover, a medical packaging paper, an embodiment of an adhesive dressing, and a medical device secured in the cover and the medical packaging paper.

With reference now to FIG. 1, an embodiment of a package 100 is shown comprising a cover 10 comprising a pocket 14 and a perimeter 12 surrounding the pocket 14. The package 100 further comprises a packaging paper 20, which may also be called a lid stock, forming a seal with the perimeter 12, and an adhesive dressing 30 coupled to the lid stock. A medical device 50 is located inside the pocket 14 of the cover 10 and sealed therein. In one example, the package 100 can be a medical device packaging or package assembly 100 that includes a cover 10, a medical packaging paper 20, a medical device 50, and an adhesive dressing 30. As shown, the medical device 50 is a catheter assembly but can be an injection needle of various types, such as epidural needle, a Seldinger needle, etc. The catheter assembly 50 of the present embodiment can include a catheter hub 51 with a catheter tube 52 attached thereto, a needle hub 55, and a needle 56 attached to the needle hub 55. A needle tip 57 of the needle 56 can be covered with a needle or protective cap 58 to prevent the needle tip 57 from puncturing the pocket 14 or medical packaging paper 20 prior to use. The package 100 is configured to keep the medical device 50 free from contaminants after packaging and prior to use. In another embodiment, the medical device 50 is an intravenous line assembly or IV set.

The cover 10, which is also known in the relevant industry as a pouch, is formed with the pocket 14 extending beyond the perimeter 12 to form a hollow space or cavity 80 to receive the medical device 50 therein. The pocket 14 is sized to enclose and accommodate at least both the medical device 50 and the adhesive dressing 30. The medical packaging paper 20 and the perimeter 12 surrounding the pocket 14 form a hermetic seal to secure the medical device 50 and adhesive dressing 30 therein and maintain a sterile environment inside the pocket 14. The cover 14 can be made of any conventional material so long as the pocket 14 remains hermetically sealed when forming the seal with the medical packaging paper 20. The cover 14 can be a thin flexible pliable material or a thick hard material. For example, the material of the cover 10 can be a transparent or translucent plastic material to permit viewing of the contents inside the pocket 14. The cover 10 can be made from a soft plastic and be pliable or from a hard plastic that maintains a shaped structure and relatively less pliable. The cover 10 is attached to the medical packaging paper 20 at the perimeter 12.

The medical packaging paper or lid stock 20 may have a release liner surface 25 facing the cover 10. The release liner surface 25 may be a surface coated with polyethylene, polypropylene, fluorocarbons, or silicone release agents. In one example, the medical packaging paper 20 comprises a multi-layer structure. For example, the medical packaging paper 20 can comprise a base layer 22 having a back surface and the release liner surface 25 opposite the back surface. The base layer 22 may be made of a plastic, fabric, fibrous material or combinations thereof. The release liner surface 25 and the back surface may have markings such as description, instructions, directions, and other desired information. The medical packaging paper 20 and the cover 10 can be sealed together at the interface between the release liner surface 25 and the perimeter 12 of the cover 10 by any sealing means, such as an adhesive, thermal fusion, or bonding.

Figure 2:
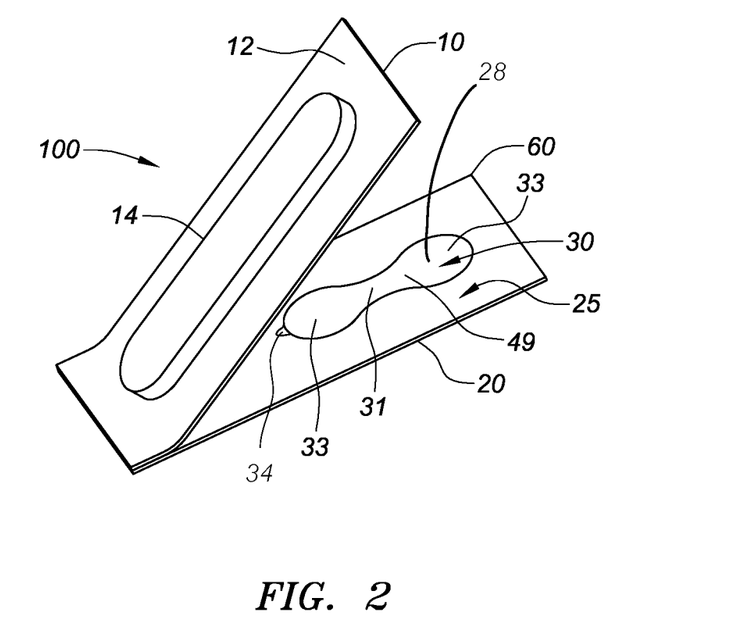
FIG. 2 is a perspective view of the medical device package of FIG. 1 with the cover partially detached from the medical packaging paper and the medical device removed.

With reference now to FIG. 2, one or more portions between the cover 10 and the medical packaging paper 20 can be free of the seal to allow the cover 10 and the medical packaging paper 20 to be pulled apart and breaking the seal, such as a peel/pull area to permit grasping and separating of the packaging paper 20 from the cover 10. For example, a corner 60 of the medical packaging paper 20 may serve as the peel/pull area. Alternatively, notches, weakened sections, or the like can be made to one or both the cover 10 and the medical packaging paper 20 to allow a user to tear the cover 10 and/or medical packaging paper 20 to allow access to the contents in the pocket 14. As shown, the cover 10 can be pulled apart from the corner 60 of the packaging paper 20 to at least partially detach the cover 10 from the lid stock 20 so that the medical device 50 can be removed and the adhesive dressing 30 on the lid stock can be accessed for use, as further discussed below.

In an example, the adhesive dressing 30 is adhered to the release liner surface 25 of the medical packaging paper 20 and positioned inside the pocket 14 when the medical packaging paper 20 is sealed to the cover 10 to maintain sterility prior to use. The adhesive dressing 30 may be compatible with EtO and gamma sterilization. The adhesive dressing 30 may be made from a breathable material, a polyester fabric, a polyurethane fabric, a foam material, or any material that can be used as a securement means to secure the medical device 50 to a surface, such as to the skin of a patient. The adhesive dressing 30 has an adhesive material or adhesive layer 35 (FIG. 3) on a bonding surface 39 of the adhesive dressing 30 that is removably attached to the release liner surface 25 of the medical packaging paper 20. The bonding surface 39 of the adhesive dressing 30 is understood to be the surface with the adhesive layer 35 and the surface that faces the device or patient during use to secure the device to a patient. The adhesive material 35 may be a medical grade, pressure-sensitive adhesive. The adhesive material 35 may be an acrylic based, silicone, or hydrocolloid adhesive. A top surface 49 of the adhesive dressing 30 opposite the bonding surface 39 can be roughened or include un-even surfaces, such as bumps or projections, to aid a user in gripping the adhesive dressing during application of the adhesive dressing 30 to the medical device 50 and a patient.

Figure 3:
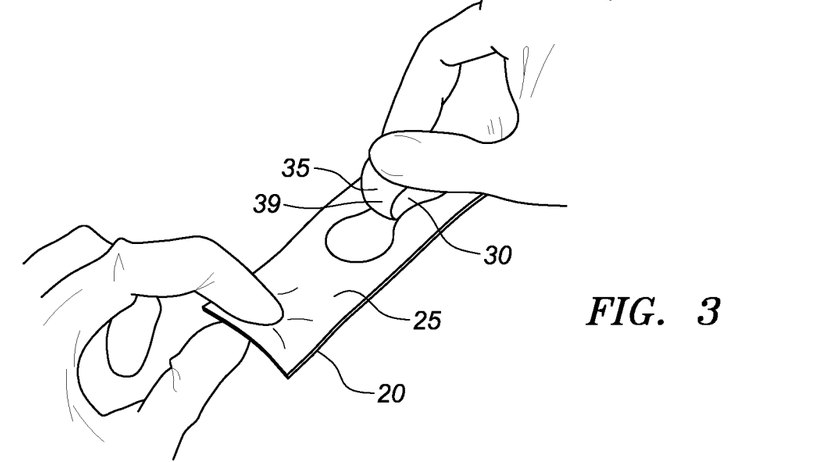
FIG. 3 is a perspective view of the adhesive dressing partially peeled away from the medical packaging paper and removed from the cover.

The adhesive dressing 30 is sized and shaped to sufficiently attach and secure the medical device 50 to, for example, a patient's skin and maintaining the device in position. As shown, the adhesive dressing 30 has a narrow region 31 transitioning into wider and larger regions 33 on opposite sides of the narrow region 31. The larger regions 33 allows a user such as a nurse to grip and secure the larger regions 33 to a patient's skin. The larger regions 33 provide a larger footprint and more adhesive than the narrow portion to secure the medical device 50 to the patient. In other examples, the adhesive dressing can embody other shapes, such as being generally rectangular. In yet other examples, the adhesive dressing is specially shaped to accommodate the medical device 50.

With further reference to FIG. 2, a dog ear 34 free of adhesive material may optionally be provided for a user to grip and remove the adhesive dressing 30 from the release liner surface 25. The dog ear 34 can extend from at least one edge of the adhesive dressing 30. As shown, the dog ear 34 extends from an edge of the larger region 33 but can extend from a different section of the outer edge. The dog ear 34 can be sized to permit a user to readily grip the adhesive dressing 30 with two fingers. A second dog ear 34 (not shown) may also be provided on the opposite end of the adhesive material 30 giving the user the option to grip either dog ear 34 when removing the adhesive dressing 35 from the release liner surface 25. Having two dog ears 34 on opposite sides of the adhesive dressing 30 can also provide the user the option to grip both dog ears 34 when applying the adhesive dressing over the medical device 50 onto the patient. This can minimize the adhesive material 35 attached to a user's fingers or gloves when removing and placing the adhesive dressing 30 onto the medical device 50 to secure the medical device 50 to the patient.

The adhesive dressing 30 may also incorporate a removable protective layer 28 attached to a top side of the adhesive dressing 30 opposite the bottom side of the adhesive dressing 30 having the adhesive material 35. The protective layer 28 may partially or completely cover the top side of the adhesive dressing 30 and can be peeled off from the adhesive dressing 30 upon the application of adhesive dressing 30 to the patient body to minimize contamination and damage to the adhesive dressing 30 during application. In other examples, the protective layer 28 can be a protective coat added to the top side, such as sprayed or applied on the top side of the adhesive dressing 30.

With reference now to FIG. 3, the lid stock 20 is shown completely detached from the cover 10. The adhesive dressing 30 is shown being peeled off or away from the medical packaging paper 20, which remains whole, i.e., in one piece, after the adhesive dressing 30 is removed. The adhesive dressing 30 can be peeled off the medical packaging paper by gripping an edge of the larger region 33 or the dog ear 34 (FIG. 2). For example, after peeling the lid stock 20 away from the cover 10 and using the medical device 50 (FIG. 1) to perform a medical procedure, such as to perform a venipuncture, the adhesive dressing 30 can then be used to secure the puncture site and the catheter hub 51 to the patient. The adhesive dressing 30 can be considered as a layer in a multi-layered packaging paper that is removable and has an adhesive layer to serve as a securement feature. In one example, more than one adhesive dressing 30 can be accommodated on the medical packaging paper 20 inside the pocket 14. For example, two elongated strips with adhesive backing may be provided with the lick stock 20. In still other examples, two or more adhesive dressing 30 of different shapes are incorporated with the lid stock, such as an elongated strip and a round adhesive dressing.

Figure 4:
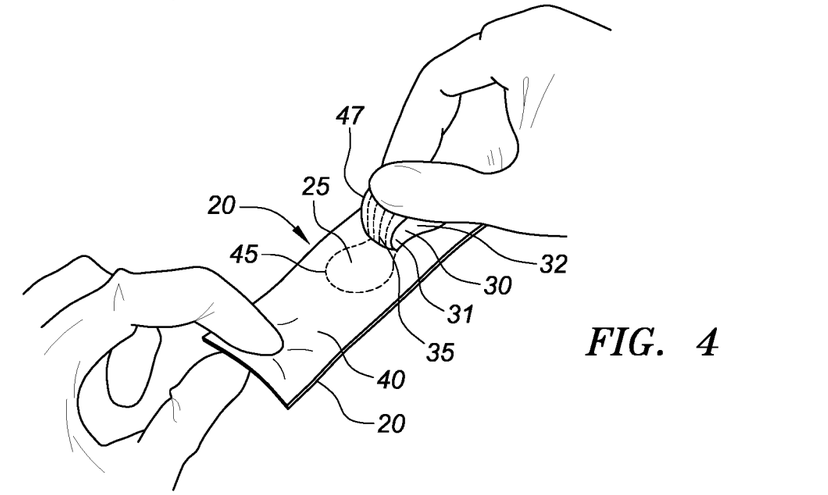
FIG. 4 is a perspective view of an adhesive dressing provided in accordance with further aspects of the present disclosure partially peeled away from the medical packaging paper and removed from the cover.

FIG. 4 illustrates an alternative lid stock 20 from an alternative medical package 100 similar to the medical package 100 of FIG. 1 except that the adhesive dressing 30 of the alternative lid stock 20 forms a portion of an adhesive dressing sheet 40 attached to the medical packaging paper 20. Said differently, the adhesive dressing 30 is formed by removing a portion of the adhesive dressing sheet 40. As shown, the adhesive dressing 30 is separable from the adhesive dressing sheet 40 by perforated lines 45, which defines a perimeter 47 of the adhesive dressing 30. The adhesive dressing 30 can be removed from the medical packaging paper 20 by tearing the perforated lines 45 and lifting the adhesive dressing 30 from the release liner surface 25. In another example, the perimeter 47 of the adhesive dressing is precut completely through the adhesive dressing sheet 40. The adhesive dressing 30 remains adhered to the release liner surface 25 until the adhesive dressing 30 is peeled off the release liner surface 25. In either configuration with perforation or complete cut-through, a void forms in the adhesive dressing sheet 40 where the adhesive dressing 30 had been removed. The adhesive dressing 30 of FIG. 4 may also have a narrow portion 31 and larger regions 33 on opposite ends of the narrow portion 31 with other shapes contemplated, such as circular, rectangular, square, etc. An adhesive material or adhesive layer 35 is provided on one side of the adhesive dressing 30 that is removably attached to the release liner surface 25. That is, the adhesive dressing 30 in FIG. 4 may be similar to the adhesive dressing 30 in FIG. 1 except that the adhesive dressing 30 in FIG. 4 is formed from the adhesive dressing sheet 40.

Figure 5:
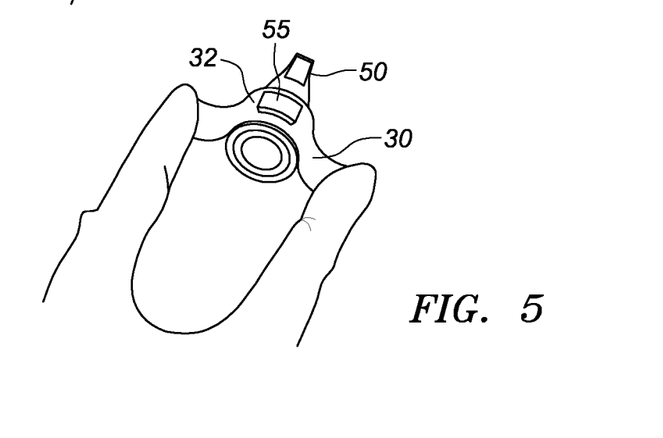
FIG. 5 is a perspective view of the adhesive dressing applied onto a medical device secured and stabilized onto a surface.

Referring now to FIG. 5, after the adhesive dressing 30 is removed from the medical packaging paper 20, the narrow region 31 is placed over the medical device 50 and the larger regions 33 are secured to the patient. An optional opening 32 is provided in the narrow region 31 of the adhesive dressing 30 to accept or accommodate a protrusion 55 on the medical device 50, such as a catheter hub, to help center and align the adhesive dressing 30 over the medical device 50 to the patient. In one example, the opening 32 may be provided in the adhesive dressing 30 when removed from the release liner surface. In another example, a perimeter of the opening 32 can be partially or completely perforated to allow the protrusion 55 to break through the opening 32 when the adhesive dressing 30 is applied onto the medical device 50.

The size and shape of the adhesive dressing 30 accompanying the medical device 50 is not limited to having a narrow region 31 with larger regions 33 on opposite sides of the narrow region 31. The size and shape of the adhesive dressing 30 and other features such as the opening 32 can be tailored according to the size, shape, contours, and/or surface features of the medical device 50.

Figure 6A:
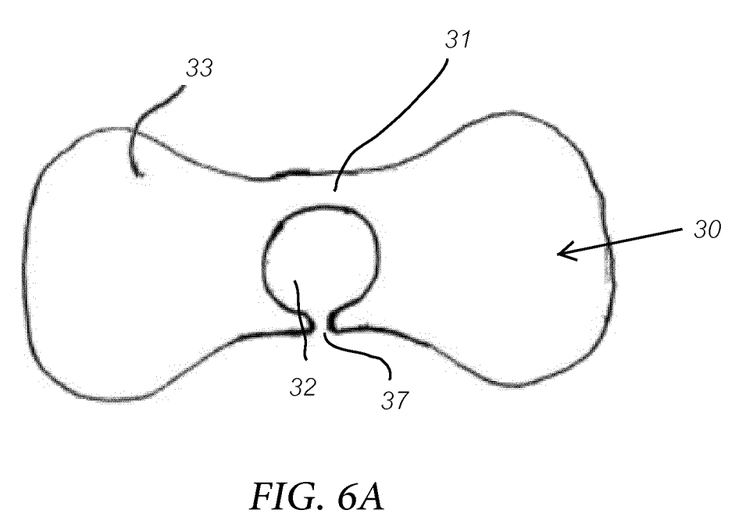
FIG. 6A is a top view of another embodiment of an adhesive dressing provided in accordance with aspects of the present disclosure.

With reference now to FIG. 6A, another embodiment of an adhesive dressing 30 is shown with an opening 32 at the narrow region 31, and a slit 37 extending from an edge of the adhesive dressing 30 to the opening 32. The opening 32 is shown with a round shape but can be any desired shape, such as square, oval, polygonal, or irregular. The slit 37 and the opening 32 can improve flexibility in handling and manipulating the adhesive dressing 30 when securing the medical device 50 to the patient. For example, the slit 37 can allow a user to widen the opening 32 to fit around the surface feature of the medical device 50, such as protrusion extending from the catheter hub 51 by gripping one or more larger regions 33 and twisting, pulling, or manipulating the ends of the adhesive dressing 30 to widen the opening 32 without tearing or damaging the adhesive dressing 30 to fit around or conform to the surface feature of the catheter hub. In one example, the medical device 50 is a ported intravenous catheter with a side port extending from a catheter hub 51. When securing the adhesive dressing 30 of FIG. 6A over the medical device 50, the opening 32 and slit 37 permits the user to apply the adhesive dressing 30 with the side port sliding through the slit 37 into the opening 32. The larger regions 33 can then be pressed onto the patient to secure and stabilize the medical device 50 to the patient.

Figure 6B:
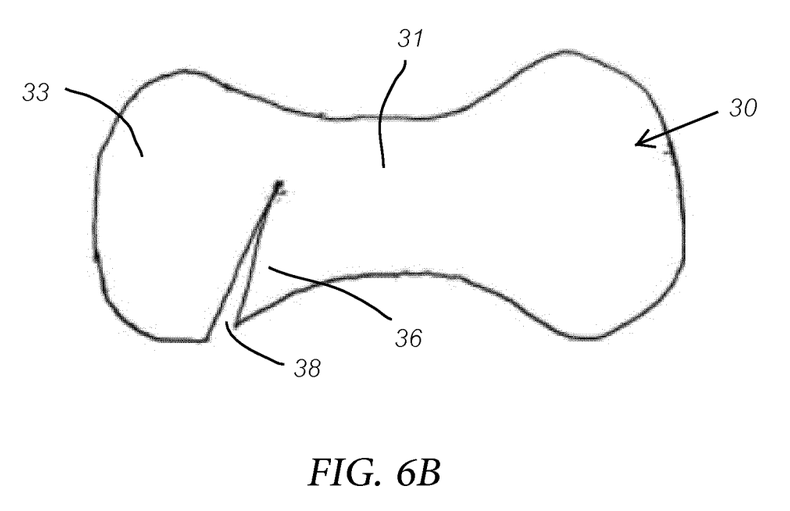
FIG. 6B is a top view of yet another embodiment of an adhesive dressing provided in accordance with aspects of the present disclosure.

FIG. 6B illustrates another embodiment of an adhesive dressing 30 provided with one or more slits or cutouts 38 extending from an edge of the adhesive dressing 30 towards the interior of the adhesive dressing 30. The adhesive dressing 30 of FIG. 6B may also include an opening and a slit for use with a ported catheter hub. The slit or cutout 38 shown forms one or more flaps 36 adjacent the cutout 38. The size and shape of the flaps 36 may depend on the path or shape of the cutout 38. For example, the path of the cutout 38 may be straight or irregular with smooth curves or piecewise continuous segments. The cutout 38 can extend in any direction along any path. In one embodiment, the cutout 38 is a set of one or more perforation lines that can be torn as the adhesive dressing 30 is secured over the medical device 50 to form the one or more flaps 36. The flaps 36 can be lifted and manipulated to accommodate contours and/or surface features of the medical device 50. In one example, the medical device 50 is an integrated tubing intravenous catheter having a port extending out a side of the catheter hub 51. When applying the adhesive dressing 30 of FIG. 6B to secure and stabilize the medical device 50 to the patient, the flap 36 can be secured over both the catheter hub 51 and the port with the tubing with the larger portions 33 pressed onto the patient.

Figure 7:
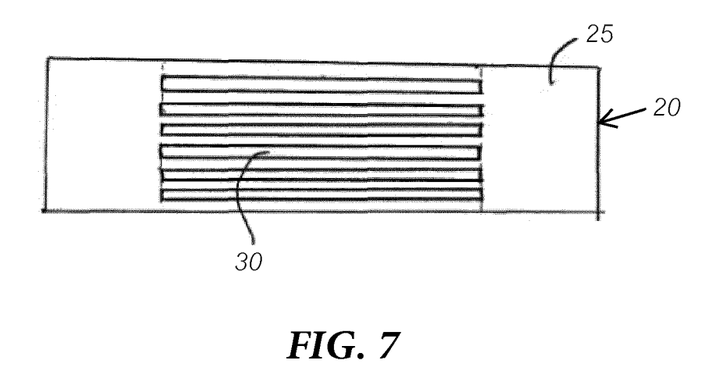
FIG. 7 is a top view of still yet another embodiment of an adhesive dressing provided in accordance with aspects of the present disclosure.

Turning now to FIG. 7, another embodiment of the adhesive dressing 30 in the form of multiple adhesive strips are adhered to the release lining surface 25 of the packaging paper 20. The adhesive strips can be provided with perforations between the strips or with a gap and be spaced from one another. The multiple strips are maintained in a sterile environment prior to use inside the perimeter 12 and preferably inside the pocket 14 of the package during packaging and storage of the medical packaging assembly 100. A user can selectively peel one or more strips from the release lining surface 25 and apply the adhesive dressing 30 in any desired fashion and location over the medical device 50. The multiple strips provide flexibility to secure and stabilize the medical device 50 to the patient. The strips are shown as thin rectangular strips but can have any size and shape.

Figure 8:
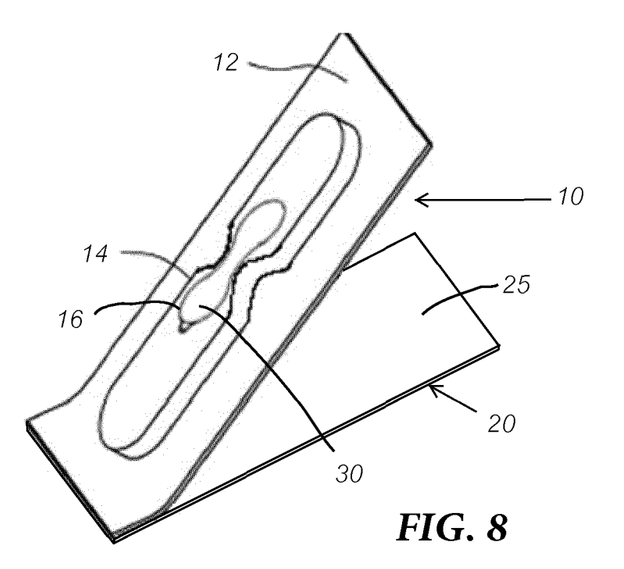
FIG. 8 is a perspective view of another embodiment of a medical device packaging assembly provided in accordance with aspects of the present disclosure.

With reference now to FIG. 8, another embodiment of a medical device packaging assembly 10 is shown and is similar to the medical device packaging assembly described above except that the adhesive dressing 30 of the present embodiment is attached to an inside surface of the pocket 14 instead of being removably adhered to the release lining surface 25 of the packaging paper 20. The adhesive dressing 30 remains in a sterile environment until the medical device packaging assembly 10 is opened.

The adhesive dressing 30 can adhere to the inside surface of the pocket 14 by a light adhesive, such as pressure-sensitive adhesive, and/or fitted inside a similarly shaped depression 16 formed in or on the pocket to hold the adhesive dressing 30 and prevent the adhesive dressing 30 from dropping off the inside surface of the pocket 14 upon peeling of the packaging paper 20 from the cover 10. The user can selectively remove the adhesive dressing 30 from the depression 16 or inside surface of the pocket 14 and apply the adhesive dressing 30 onto the medical device 50 and patient. In one example, the adhesive dressing 30 is removed from the pocket 14, a removable lining surface can remain attached to the adhesive dressing 30 thereby allowing the removable lining surface to be removed from the adhesive dressing 30 when needed. In another example, the removable lining surface can remain attached to the inside surface of the pocket 14 when the adhesive dressing 30 is peeled off from the removable lining surface. In yet another example, the inside surface of the pocket is the removable lining surface.

Figure 9:
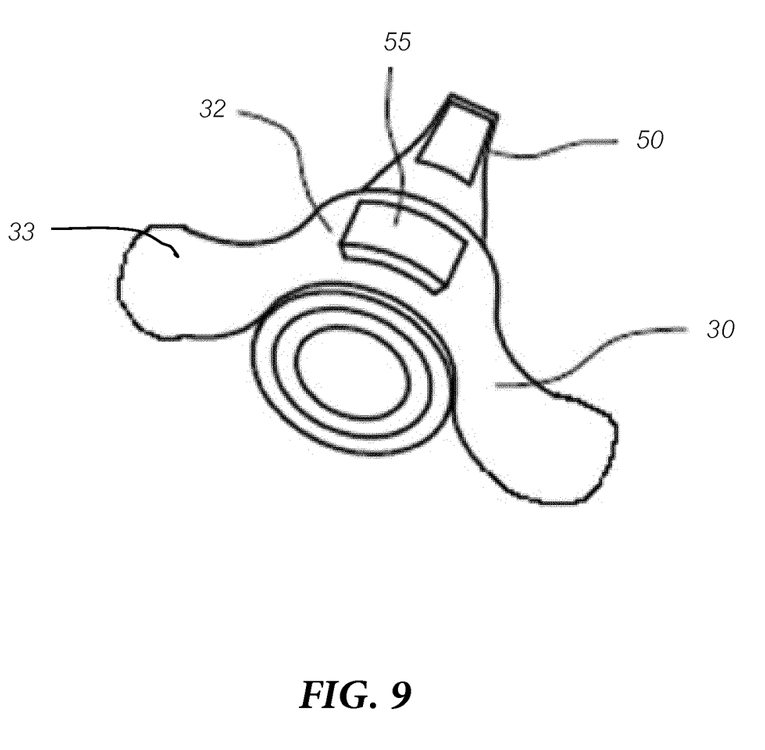
FIG. 9 is a perspective view of yet another embodiment of a medical device packaging assembly provided in accordance with aspects of the present disclosure.

With reference now to FIG. 9, a perspective view of yet another embodiment of an adhesive dressing 30 is shown placed over a medical device 50. In the present embodiment, the adhesive dressing 30 is already attached or pre-attached to the medical device 50 when packaged inside a medical device package, such as the medical device package 100 of FIG. 1. Thus, when the package 100 is separated to remove the medical device 50, the adhesive dressing 30 is already attached to the body thereof. As shown, the adhesive dressing 30 is attached to the medical device 50 with a protrusion or feature 55 on the medical device 50 extending through an opening 32 of the adhesive dressing 30. In addition to being attached to the medical device when inside the packaging 100, large regions 33 of the adhesive dressing 30 can be removably attached to the release lining surface 25 of the packaging paper 20 so that when the packaging paper 20 is removed, the large regions 33 separate from the releasing lining surface and ready for placement against a patient. Alternatively, the large regions 33 of the adhesive dressing 30 can be equipped with removable lining surfaces that can be removed when the adhesive dressing 30 is ready to be applied to secure and stabilize the medical device 50 to the patient. In still other examples, the exterior surface of the medical device 50 can be coated with a release surface or be provided with a release surface and the large regions 33 of the adhesive dressing 30 attached directly to the surfaces of the medical device.

A method of making the medical device package 100 includes first providing a cover 10, a medical packaging paper 20, one or more medical devices 50, and one or more adhesive dressings 30. The cover 10 has a pocket 14 and a perimeter 12 surrounding the pocket 14. The medical device 50 and adhesive dressing 30 are located within the pocket 14 to maintain sterility before use. The adhesive dressing 30 can be a single unit removably attached to a release lining surface 25 of the medical packaging paper 20 or can be a portion of an adhesive dressing sheet 40 removably attached to the release lining surface 25. An opening 32 can be provided in the adhesive dressing 30 to engage with a protrusion or feature 55 on the medical device 50. The medical packaging paper 20 is hermetically sealed to the perimeter 12 of the cover 10 by adhesive, thermal fusion, or bonding, to hermetically seal the medical device 50 and dressing 30 therein, forming the medical package 100.

A method of securing the medical device 50 to a surface, such as to a patient's skin includes removing the cover 10 from the medical packaging paper 20 until the medical device 50 and the adhesive dressing 30 are accessible. The medical device 50 is removed from the medical package 100 and placed on a surface or the patient. The adhesive dressing 30 is peeled off the release lining surface 25 and placed over the medical device 50 and attached to the patient. The opening 32 can be fitted over the protrusion 55 of the medical device 50 to align the adhesive dressing 30 over the medical device 50 and the patient to ensure enough of the adhesive dressing 30 attaches to the patient.

The medical device package 100 can be used for any application in which a device is to be packaged and a securing means is integrated into the packaging material. This arrangement provides less material, less waste that translates to cost savings and environmentally friendly. As this arrangement efficiently packages the components in a quick and simple manner, this saves the user's time from gathering different components needed to perform their job. Additionally, this also prevents a user from losing any of the contents inside the package.

Thus, as described, a medical device package or packaging assembly is provided comprising a lid stock attached to a pouch and sealing a medical device inside an interior cavity of the pouch. The lid stock has an exterior surface and an interior surface relative to the interior cavity of the pouch and wherein one or more adhesive dressing is secured to a release liner on the interior surface of the lid stock. In some examples, the lid stock comprises a multi-layer structure that can include a cut-out, a perforation, a release liner, an adhesive layer adhered to the release liner, an adhesive dressing, or combinations thereof. The medical device can be a catheter assembly with a valve, a tip protector, a valve opener, or combinations thereof.

Although limited embodiments of the medical packaging assemblies and their components have been specifically described and illustrated herein, many modifications and variations will be apparent to those skilled in the art. Furthermore, elements and features expressly discussed for one embodiment but not for another may equally apply provided the functionality or structures do not conflict. Thus, unless the context indicates otherwise, like features for one embodiment are applicable to another embodiment. Accordingly, it is to be understood that the medical package, cover, medical packaging paper, and adhesive dressing and their components constructed according to principles of the disclosed devices, systems, and methods may be embodied other than as specifically described herein. The disclosure is also defined in the following claims.

What is claimed is:

1. A combination catheter assembly and packaging assembly comprising:
   a cover comprising an inside surface defining a pocket and a perimeter extending outwardly from a perimeter of the pocket;
   a packaging paper with a release liner surface peelably affixed to the cover, the packaging paper forming a hermetical seal with the perimeter of the cover around the pocket and capturing a catheter assembly at least partially inside the pocket such that the catheter assembly is directly exposed to the inside surface of the cover, the catheter assembly comprising a catheter hub having a catheter tube extending from the catheter hub and a needle hub having a needle extending from the needle hub; and
   a strip of adhesive dressing having an adhesive layer located within a space defined by the pocket and the packaging paper and separated from the catheter assembly, the strip of adhesive dressing is located between the cover and the catheter assembly and separable from the cover or between the packaging paper and the catheter assembly and separable from the packaging paper.

2. The combination of claim 1, wherein the catheter assembly comprises a needle guard having a surface located to a side of the needle in a ready to use position.

3. The combination of claim 2, wherein the strip of adhesive dressing has a narrow region located between two regions that are wider than the narrow region.

4. The combination of claim 3, wherein the strip of adhesive dressing is compatible with EtO and gamma sterilization.

5. The combination of claim 2, wherein the strip of adhesive dressing is made from a breathable material, a polyester fabric, a polyurethane fabric, or a foam material.

6. The combination of claim 1, wherein the strip of adhesive dressing is removably attached to the packaging paper.

7. The combination of claim 6, wherein the release liner surface contacts the strip of adhesive dressing.

8. The combination of claim 7, wherein the release liner surface is a surface coated with polyethylene, polypropylene, fluorocarbons, or silicone release agents.

9. The combination of claim 7, further comprising an adhesive dressing sheet attached to the release liner surface of the packaging paper, wherein the strip of adhesive dressing forms a portion of the adhesive dressing sheet and wherein the adhesive dressing sheet is removably adhered to the packaging paper.

10. The combination of claim 9, wherein the strip of adhesive dressing is attached to the adhesive dressing sheet along perforated lines, and the strip of adhesive dressing is configured to separate from the adhesive dressing sheet along the perforated lines.

11. The combination of claim 6, wherein the adhesive material is a medical grade, pressure-sensitive adhesive.

12. The combination of claim 11, wherein the adhesive material is an acrylic based, silicone, or hydrocolloid adhesive.

13. The combination of claim 6, wherein the strip of adhesive dressing has an opening matching a shape of a protrusion on the catheter hub.

14. The combination of claim 13, wherein the strip of adhesive dressing has two flaps and wherein perforations are provided with the packaging paper defining the two flaps when the strip of adhesive dressing is separated.

15. A method of making a combination catheter assembly and packaging assembly, the method comprising:
   providing a cover comprising an inside surface defining a pocket, a pocket perimeter and a cover perimeter extending outwardly from the pocket perimeter;
   providing a packaging paper;
   providing a catheter assembly comprising a catheter hub having a catheter tube extending from the catheter hub and a needle hub having a needle extending from the needle hub and a strip of adhesive dressing within the of the pocket of the cover, the strip of adhesive dressing being separated from the catheter assembly;

forming a seal between the cover perimeter and the pocket perimeter of the cover and the packaging paper;

wherein the catheter assembly and the strip of adhesive dressing are hermetically sealed within a space defined by the pocket and the packaging paper and the catheter assembly is directly exposed to the inside surface of the cover; and wherein the strip of adhesive dressing is located between the cover and the catheter assembly and separable from the cover or between the packaging paper and the catheter assembly and separable from the packaging paper.

16. The method of claim 15, wherein the catheter assembly comprises a needle guard having a surface located to a side of the needle.

17. The method of claim 15, further comprising placing the strip of adhesive dressing around the catheter hub and securing the catheter hub to a surface.

18. The method of claim 15, wherein the strip of adhesive dressing is compatible with EtO and gamma sterilization.

19. The method of claim 18, wherein the strip of adhesive dressing is made from a breathable material, a polyester fabric, a polyurethane fabric, or a foam material.

20. The method of claim 18, wherein the strip of adhesive dressing is removably attached to the medical packaging paper.

21. The method of claim 18, wherein the medical packaging paper comprises a release liner surface contacting the strip of adhesive dressing.

22. The method of claim 21, wherein the release liner surface is a surface coated with polyethylene, polypropylene, fluorocarbons, or silicone release agents.

23. The method of claim 21, further comprising an adhesive dressing sheet removably adhered to the release liner surface of the medical packaging paper, wherein the strip of adhesive dressing is a portion of the adhesive dressing sheet and is removably adhered to the medical packaging paper.

24. The method of claim 23, wherein the strip of adhesive dressing is attached to the adhesive dressing sheet along perforated lines, and the strip of adhesive dressing is configured to separate from the adhesive dressing sheet along the perforated lines.

25. The method of claim 20, wherein the adhesive material is a medical grade, pressure-sensitive adhesive.

26. The method of claim 25, wherein the adhesive material is an acrylic based, silicone, or hydrocolloid adhesive.

27. The method of claim 20, wherein the strip of adhesive dressing has an opening matching a shape of a protrusion on the catheter hub.

28. The method of claim 27, wherein the strip of adhesive dressing has two flaps and wherein perforations are provided with the packaging paper defining the two flaps when the strip of adhesive dressing is separated.

29. A combination catheter assembly and packaging assembly comprising:

a cover with a single pocket, a pocket perimeter, and a cover perimeter extending outwardly from the pocket perimeter; the single pocket comprising a first side a second side, and an inside surface;

a packaging paper peelably affixed to the cover, the packaging paper forming a hermetical seal with the cover around the single pocket and capturing a catheter assembly at least partially inside the single pocket such that the catheter assembly is directly exposed to the inside surface of the cover;

a strip of adhesive dressing having an adhesive layer located within a space defined by the single pocket and the packaging paper separated from the catheter assembly, and separable from the packaging paper;

wherein the strip and of adhesive dressing catheter assembly are located inside the single pocket immediately adjacent the first side and the second side; and wherein the catheter assembly comprises a catheter hub with a catheter tube and the needle projects through the catheter hub and the catheter tube.

30. The combination of claim 29, wherein the strip of adhesive dressing is located between the cover and the catheter assembly or between the packaging paper and the catheter assembly.

31. The combination of claim 29, further comprising a needle guard located inside the catheter hub.

32. The combination of claim 31, wherein the strip of adhesive dressing a narrow region located between two regions that are wider than the narrow region.

* * * * *